US00RE39705E

(19) United States
(12) Reissued Patent
Keller et al.

(10) Patent Number: US RE39,705 E
(45) Date of Reissued Patent: Jun. 26, 2007

(54) METHOD OF TREATING GLUTATHIONE DEFICIENT MAMMALS

(75) Inventors: Robert H. Keller, Weston, FL (US); David Kirchenbaum, Weston, FL (US)

(73) Assignee: Vit-Immune, L.C., Hollywood, FL (US)

(21) Appl. No.: 09/994,164

(22) Filed: Nov. 26, 2001

Related U.S. Patent Documents

Reissue of:
(64) Patent No.: 6,262,019
Issued: Jul. 17, 2001
Appl. No.: 09/302,217
Filed: Apr. 29, 1999

U.S. Applications:
(60) Provisional application No. 60/083,661, filed on Apr. 30, 1998.

(51) Int. Cl.
*A01N 37/18* (2006.01)
*A61K 38/02* (2006.01)

(52) U.S. Cl. ..... 514/12; 514/7; 514/21; 514/23; 514/251; 514/276; 424/49; 424/54; 424/535; 424/655; 530/365; 530/833

(58) Field of Classification Search ..... None
See application file for complete search history.

(56) References Cited

U.S. PATENT DOCUMENTS

| | | | |
|---|---|---|---|
| 4,256,760 | A | 3/1981 | Los |
| 4,277,496 | A | 7/1981 | Los |
| 4,292,403 | A | 9/1981 | Duermeyer |
| 5,290,571 | A | 3/1994 | Bounous et al. |
| 5,456,924 | A | 10/1995 | Bounous et al. |
| 5,696,109 | A | 12/1997 | Malfroy-Camine et al. |

OTHER PUBLICATIONS

"Screening of Potential Chemropreventive Agents Using Biochemical Markets of Carcinogenesis" by Sheela Sharma, Jill D. Stutzman, Gary J. Kelloff and Vernon E. Steele, Cancer Research 54, 5848–5855, Nov. 15, 1994.
Low Blood Glutathione Levels in Healthy Aging Adults, pp. 720–725, Calvin A. Long, et al.
a–Lipoic Acid: Biological Effects and Clinical Implications, pp. 177–183, Trent W. Nichols, Jr. M.D.
Glutathione: Systemic Protectant Against Oxidative and Free Radical Damage, pp. 155–171, 173–176, Parris M. Kidd, Ph.D.
Importance and Regulation of Hepatic Glutathione, pp. 251–266, Laurie D. Deleve, M.D., Ph.D. et al.
Probiotics in Human Medicine, pp. 439–442, R. Fuller.
Aids Wasting Syndrome as an Entero–Metabolic Disorder: The Gut Hypothesis, pp. 40–45, 47–53, Mitchell Kaminski, Jr., M.D., et al.
The Effects of L–Glutamine, N–Acetyl–D–Glucosamine, Gamma–Linolenic Acid and Gamma–Oryzanol on Intestinal Permeability.
PROMT on STN, Information Access Company, 1998: 1310, BioDynamax Supplement—Ultra Antioxidants Tablets, Product Alert (Dec. 22, 1997) ISSN: 0740–3801.*

* cited by examiner

*Primary Examiner*—Robert A. Wax
(74) *Attorney, Agent, or Firm*—Frommer Lawrence & Haug LLP; Ronald R. Santucci

(57) ABSTRACT

Glutathione (GSH) is a tripeptide of extreme importance as a catalyst, reductan, and reactant. It can be depleted intracellularly either by forming a direct complex with an electrophilic agent (accomplished investigationally by agents such as bromobenzene or diethyl maleate), by way of inhibition of synthesis, or by subjecting cells to oxidant stress. Most cells, except for epithelia cells, do not have a direct transport capacity for intact GSH. Non-epithelial cells must either transport precursor substrates for GSH synthesis or salvage amino acids from circulating GSH for reuse in intracellular resynthesis. Dietary cysteine is a rate limiting substrate for the synthesis of glutathione and also inhibits GSH efflux. Although GSH is synthesized from precursors in virtually all cells, the liver is the main source of plasma GSH. Protection and support of liver function is paramount to elevating GSH levels. The disclosure is also of a unique combination of nutritional supplements including n-acetyl cysteine, vitamin C, 1-glucosamine, n-acetyl d-glucosamine, quercitin, sylimarin, Alpha lipoic acid and high protein, low fat whey that are combined to support various bodily systems involved in glutathione synthesis, reutilization and storage; all intended to elevate glutathione concentration in the mammalian cell.

6 Claims, No Drawings

METHOD OF TREATING GLUTATHIONE DEFICIENT MAMMALS

Matter enclosed in heavy brackets [ ] appears in the original patent but forms no part of this reissue specification; matter printed in italics indicates the additions made by reissue.

[This application claims the benefit of Provisional No. 60/083,661 filed Apr. 30, 1998.] *This application is a Reissue of Ser. No. 09/302,217, filed Apr. 29, 1999, now U.S. Pat. No. 6,262,019, which claims benefit of provisional application 60/083,661, filed Apr. 30, 1998.*

BACKGROUND OF THE INVENTION

1. Field of the Invention

This invention provides a method of improving glutathione (GSH) concentrations, both intra and extracellularly, in mammals, thereby improving the cellular and humoral immune response. It comprises oral administration of a therapeutically effective amount of nutritional supplement which is composed of critical and synergistic quantities of amino acids, peptides, and bioflavanoids.

2. Brief Description of Related Art

Glutathione is a well-known tripeptide, which exists in two basic forms. The antioxidant form or "reduced glutathione" tripeptide is conventionally called "glutathione" and abbreviated as "GSH". The oxidized form is a sulfur-sulfur linked compound known as glutathione disulfide (GSSG).

Glutathione in its biologically active, reduced form (GSH) has the formula:

(1)

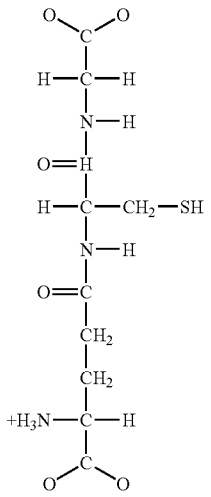

and is appropriately named γ-L-Glutamyl-L-cysteinylglycine. It is ubiquitous in animals, plants, and microorganisms and being water soluble is found mainly in the cell cytosol and other aqueous phases of the living system. Glutathione often attains millimolar levels inside living cells, which makes it one of the most highly concentrated intracellular antioxidants.

Glutathione is homeostatically controlled, both inside the animal cell and outside. Enzyme systems synthesize it, utilize it, and regenerate it per the gamma-glutamyl cycle. (Meister A. Glutathione, Ascorbate and Cellular Protection Cancer Res (Suppl) 1994 (Apr 1); 54:1969S–1975S).

Glutathione is most concentrated in the mammal liver (10 mM), where the P450 Phase II" enzymes require it to convert fat-soluble substances into water-soluble GSH conjugates in order to facilitate their excretion. While providing GSH for their specific needs, the liver parenchymal cells export GSH to the outside, where it serves as systemic source of-SH/reducing power.

Briefly, glutathione synthesis occurs within animal cells in two closely linked enzymatically controlled reactions that utilize Adenosine Triphosphate (ATP) and draw on nonessential amino acids as substrates. First, cysteine and glutamate are combined (by the enzyme gamma-glutamyl cysteinyl synthetase, with availability of cysteine usually being the rate-limiting factor. Cysteine is generated from the essential amino acid methionine, from the degradation of dietary protein, or from turnover of endogenous proteins. The buildup of GSH acts to feedback-inhibit this enzyme, thereby helping to ensure homeostatic control over GSH synthesis.

The second GSH synthesis reaction combines gamma-glutamylcysteine with glycine to generate GSH (catalyzed by GSH synthetase).

With regard to the essentiality of GSH for the survival of the mammal, substantial information is available from studies on hereditary GSH depletion in the human, and from experimental depletion and repletion of GSH in animal models and cell cultures, see for example: Meister A. Larsson A. Glutathione Synthetase Deficiency and Other Disorders of the Gamma-Glutamyl Cycle; Scriver CR. et al eds. The Metabolic and Molecular Bases of Inherited Disease (Volume I). New York: McGraw-Hill: 1995:1461–1495 (Chapter 43); and Beutler E. Nutritional and Metabolic Aspects of Glutathione, Annu Rev Nutr 1989;9:287–302.

Reduced GSH levels in mammalian cells are associated with a wide variety of pathophysiologic states, including hepatic dysfunction, malignancies, HIV infection, pulmonary disease, Parkinson's disease, related immunologic illnesses and physiological conditions; see for example the descriptions in Kidd, Alternative Medicine Review, Vol. 2, No. 3, pages 156–176 (1997).

The consequences of sustained GSH depletion are fatal. As cellular GSH is depleted, first individual cells die in those areas most affected. Then zones of tissue damage begin to appear. Localized free-radical damage spreads across the tissue in an ever-widening, self-propagating wave.

An object of this invention is to promote gastrointestinal absorption and intracellular uptake of components which will maximize intracellular reduced glutathione production by a mammal including a human.

SUMMARY OF THE INVENTION

The invention comprises a composition of matter, which comprises in admixture:

N-acetylcysteine;

vitamin C; and a pharmaceutically acceptable systemic carrier for oral administration.

In preferred embodiments, the invention further comprises one or more of the following:

alpha-lipoic acid;

sylmarin;

quercitin;

1-glutamine;

N-acetyl-d-glucosamine;

a probiotic.

The invention also comprises systemic administration of the composition of the invention to a mammal suffering from low glutathione levels, to stimulate the natural production of glutathione in the biological cells of the mammal.

The term "low glutathione levels" as used herein means a blood glutathione level below about 440 μg glutathione/$10^{10}$ erythrocytes, determined by the colorimetric method of Beutler et al., Improved Method for the Determination of Blood Glutathione, J. Lab. Clin. Med., 61;882–8(1963). Normal levels in humans ranges from about 440 to 654 μg/$10^{10}$ erythrocytes.

DETAILED DESCRIPTION OF THE PREFERRED EMBODIMENTS OF THE INVENTION

Recently, there have been many scientific papers published discussing the direct relationship between decreased glutathione levels and the progression of many chronic diseases. Glutathione functions as an antioxidant, antitoxin and protector of red blood cells, and is extremely important to the immune system. It neutralizes free radicals minimizing the damage they cause and is profoundly important for cellular homeostasis.

As with other cell types, the proliferation, growth, and differentiation of immune cells is dependent on GSH. Both the T and the B lymphocytes require adequate levels of intracellular GSH to differentiate, and healthy humans with relatively low lymphocyte GSH were found to have significantly lower CD4 counts; Kinscherf R. Fischbach T. Mihm S. et al. Effect of glutathione depletion and oral N-acetylcysteine treatment on CD4+ and CD8+ cells. FASEB J 1994;8:448–451. Intracellular GSH is also required for the T-cell proliferative response to mitogenic stimulation, for the activation of cytotoxic T "killer" cells, and for many specific T-cell functions, including DNA synthesis for cell replication, as well as for the metabolism of interleukin-2 which is important for the mitogenic response; Wu D. Meydani S N, Sastre J. et al. In-vitro glutathione supplementation enhances interleukin-2 production and mitogenic response of peripheral blood mononuclear cells from young and old subjects; J Nutr 1994;124:655–663.

In summary, it has been demonstrated that decreased levels of glutathione may be a result of various types of prolonged stress, increased free radical formation and hyperactivity of the immune system. These factors in turn compromise the health of mammalian cells. Despite the apparent importance of adequate glutathione levels, little emphasis has heretofore been placed on replacing depleted stores. Some glutathione comes from the diet but the majority is made in the liver.

Studies have demonstrated that oral glutathione supplementation is not well absorbed by many of the mammal's cells and does not replenish losses inside cells where it is most needed; Witschi A. Reddy S. Stofer B. et al. The systemic availability of Oral Glutathione. Eur. J Clin. Pharmacol. 1992;43:667–669.

The sulfur-containing amino acid 1-cysteine is the precursor that most limits the cellular biosynthesis of GSH. When substituted into the diet in place of the total protein allowance it was effective in raising GSH levels (see Witschi et al., supra.)

Glutathione esters, synthetic compounds prepared by linking the glycol end of GSH into ester bonds, have been the subject of much research by Meister, Anderson, supra., as potential oral GSH delivery compounds (see also U.S. Pat. No. 4,784,685). These esters do appear to be effective GSH delivery vehicles, but have the disadvantage that they yield alcohols in vivo when their ester bonds are broken, and their safety over the long term has yet to be satisfactorily demonstrated.

We have discovered that to efficiently raise the level of glutathione intracellularly, it is necessary to employ several different mechanisms that work simultaneously. First, essential elements needed by the body for the manufacture of glutathione must be introduced. Second, gastro-intestinal health of the mammal must be optimal to facilitate nutrient absorption. Third, the liver function must be supported and protected as the liver is the glutathione "manufacturing and storage house". Lastly, recycling existing glutathione and enhancing enzymatic reactions that promote glutathione synthesis are also important functions which are advantageous to support.

The essential element needed by the mammalian cell to manufacture glutathione (GSH) is N-acetylcysteine (NAC). It has proven to be the most efficient dietary source of glutathione precursor. It is a precursor and the main limiting factor necessary for the body to manufacture reduced glutathione. NAC is well absorbed by the intestine and readily converted by the mammalian cell (particularly in the liver) to glutathione.

The absorption of N-acetylcysteine (NAC) and transport across the cellular membrane is facilitated by the presence of ascorbic acid (vitamin C). Vitamin C maximizes NAC transport across biological cell membranes and helps to conserve existing glutathione stores within the cell cytosol.

The utilization of N-acetylcysteine within the biological cell to synthesize glutathione is improved by the presence of alpha lipoic acid. Alpha lipoic acid increases the cell's ability to make glutathione. It enables the key enzyme required for glutathione synthesis to work under optimum conditions and induces a substantial increase in intracellular reduced glutathione; see Busse E. Zimmer G. Schopohl B, et al. Influence of alpha-lipoic acid on intracellular glutathione in vitro and in vivo; Arzneimittel-Forschung 1992;42:829–831; and Han D. Handelman G. Marcocci, et al. Lipoic Acid Increases de novo Synthesis of Cellular Glutathione by Improving Cystine Utilization, Biofactors 1997;6:321–338. 1995:29: 1263–73.

As mentioned above, support of liver function in the mammal being treated for low glutathione levels is advantageous. For this purpose, there may be orally administered to the mammal the following:

A. Sylimarin serves to improve and restore liver function. It quenches free radicals, reduces potential toxicity, and stimulates protein synthesis necessary to create new liver cells. Also known as "silibin", "silybin" or "silybinin", Silymarin is a generic term for extract from the mature fruits of Silybum marianum (sometimes Carduus marianus), commonly known as milk thistle; see Madaus AG publication: Legalon. Koln, Germany, 1989 and Valenzuela A, et al. Silymarin Protection Against Hepatic Lipin Peroxidation Induced by Acute Ethanol Intoxication in Rats, Biochemical Pharmacology, 1985:34(12):2209–2212. Sylimarin is available under the trade name Legalon®, from Madaus AG, (Jarrow Formulas, Inc.; Madaus, 1989).

B. Quercetin [2-(3,4-Dihydroxyphenyl)-3,5,7-trihydroxy-4H-1-benzopyran-4-one] is used for its ability to eliminate toxic compounds found in the liver. It has anti-hepatotoxic, antiviral, anti-inflammatory and antibacterial properties. It may be synthesized by the method of Shakhova et al., Zh. Obsheh. Khim., 32, 390 (1962).

Advantageously, the following nutritionals are also employed in the method of the invention.

L-glutamine is an essential dietary component for the support of gastrointestinal growth and function and it is utilized as fuel in the small intestines. It is used by the intestinal tract in large amounts for energy during periods of physiological stress. It has been shown to preserve liver glutathione after lethal hepatic injury and nourish tissues in the GI tract, liver and immune system, see for example; Souba, W.W., et al. The Role of Glutamine in Maintaining a Healthy Gut and Supporting the Metabolic Response to Injury and Infection. J. Of Surgical Res., 990:48(4):83–91.

N-acetyl-d-glucosamine (NAG) is a key precursor in the biosynthesis of mucosal glycoproteins that form glycocalyx. The glycalyx is the most superficial, highly viscous layer of the gut mucosa that comes in contact with intestinal contents. The glycoprotein layer acts to protect the underlying tissues from exposure to enzymes, acid and bacterial assault while providing a selectively absorptive surface, Wilmore, D. W., et al, The gut: a Central Organ After Surgical Stress; Surgery 1988: 104, (5):917–23.

Probiotics or "healthy bacteria" are necessary as they breakdown nutrients, eliminate toxins and inhibit harmful bacteria that enter mammalian systems through the GI tract. The term "Probiotic" is defined herein as "A live microbial food supplement which beneficially affects the host mammal by improving its microbial balance". Representative of healthy bacteria are isolates of bifidobacteria, lactobacilli, such as Lactobacillus acidophilus and Lactobacillus casei, propionibacteria, and enterococci. Lactobacilli are preferred in the composition and method of the invention (see Perdigon, G. et al., Immunology 63:17–23 (1988)). More preferably Lactobacillus rhamnosus, Lactobacillus casei, Bifidobacterium longum, Bifidobacterium infantis, Lactobacillus acidophillus, and Saccharomyces boulardi are used.

Finally, a source of dietary protein is preferred and advantageous to supplement the nutritional needs of the mammal. We have found that the compositions of the invention and the method herein described are optimized by inclusion of a biologically active whey protein composition comprising an undenatured whey protein concentrate obtained from raw mammalian milk. This concentrate contains substantially all of the heat labile whey protein found in the raw milk. Representative of concentrate which are commercially available include Promod™, available from Ross Laboratories, Division of Abbott Laboratories, Chicago, Ill. Concentrates may also be prepared by the method described in U.S. Pat. No. 5,290,571, incorporated herein by reference thereto. The undenatured whey protein concentrates also contain a rich variety of immunoglobulins which boast the immunologic response of the mammal treated with the concentrates; see for example U.S. Pat. No. 5,456,924 which is incorporated herein by reference thereto.

A high protein, low fat whey has immuno-supportive properties. It is rich in naturally active immunoglobulins, essential amino acids and other important nutrients critical for proper nutrient utilization within the gut.

We have discovered that the ingredients described above work synergistically to provide the necessary nutrients required for glutathione production while supporting the mammal's ability to produce and preserve existing stores of GSH. The effect of the admixture of ingredients is far more significant than the individual ingredients alone.

This invention also relates also to pharmaceutical dosage unit forms for systemic administration (oral, topical administration) which are useful in treating mammals, including humans. The term "dosage unit form" as used in this specification and in the claims refers to physically discrete units suitable as unitary dosage for mammalian subjects, each unit containing a predetermined quantity of the essential active ingredient; calculated to produce the desired effect in combination with the required pharmaceutical means which adapt said ingredient for systemic administration. Examples of dosage unit forms in accordance with this invention are tablets, capsules, orally administered liquid preparations in liquid vehicles, suppositories, and dry preparations for the extemporaneous preparation of preparations in a liquid vehicle. Solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn syrup, corn starch, talc and the like. Capsules, both hard and soft, are formulated with conventional diluents and excipients, for example, edible oils, talc, calcium carbonate, calcium stearate, magnesium stearate and the like. Liquid pharmaceutical preparations for oral administration may be prepared in water or aqueous solutions which advantageously contain suspending agents, such as for example, sodium carboxymethylcellulose, methylcellulose, acacia, polyvinyl pyrrolidone, polyvinyl alcohol and the like.

Such preparations must be stable under the conditions of manufacture and storage, and ordinarily contain in addition to the basic solvent or suspending liquid, preservatives in the nature of bactericidal and fungicidal agents, for example, parabens, chlorobutanol, benzyl alcohol, phenol, thimerosal, and the like. In many cases it is preferable to include isotonic agents, for example, sugars or sodium chloride. Carriers and vehicles include vegetable oils, water, ethanol, and polyols, for example, glycerol, propylene glycol, liquid polyethylene glycol, and the like.

The pharmaceutical dosage unit forms are prepared in accordance with the preceding general description to provide an effective amount of the essential active ingredient per dosage unit form in admixture with the means for adaptation to systemic administration. In general, the unit dose form will contain 3 to 73 percent by weight of the essential active ingredient.

It will be appreciated that the exact dosage of the essential active ingredient constituting an effective amount for treatment of a mammal according to the method of the invention will vary greatly depending on the specific nature of the clinical condition being treated, severity of the condition, species of mammal, age, weight and condition of the mammal, mode of administration of the dosage form and the specific formulation being administered. The exact dose required for a given situation may be determined by administration of a trial dose and observation of the clinical response. In general, an effective amount to be administered will be within a range of from about 0.1 mg. per kg. to about 50 mg. per kg. of body weight of the recipient, daily. Preferably 0.5 mg./kg. to about 25 mg./kg. daily is provided. In most instances, a single month of administration will effect a noticeable response and bring about the result desired. In cases such as the treatment of immunological conditions however, it may be desirable to repeat the administrations several times daily over longer periods of time.

The following examples and preparations describe the manner and process of making and using the invention and set forth the best mode contemplated by the inventor of carrying out the invention but are not to be construed as limiting.

EXAMPLE 1

A mixture of the following ingredients is prepared by hand mixing:

| Ingredient | Quantity |
|---|---|
| N-acetylcysteine | 1,000 to 20,000 mg |
| vitamin C | 5,000 to 50,000 mg |
| alpha-lipoic acid | 100 to 2,500 mg |
| sylmarin | 100 to 2,500 mg |
| Quercetin | 100 to 2,500 mg |
| l-glutamine | 500 to 2,000 mg |
| N-acetyl-d-glucosamine | 500 to 2,000 mg |
| whey protein concentrate | 1,000 to 20,000 mg |
| *Lactobacillus acidophilus* Twenty Million to One Billion CFU: Schiff Products, Inc., Salt Lake City, Utah. | |
| orange essence flavor | Adjust to taste |

The mixture which constitutes the essential active ingredient of a preferred embodiment of the invention, together with a flavorant may be compounded into wafers, tablets or capsules containing 750 to 14,000 mg of active ingredient. In an uncompounded form, the powder dry mixture may be orally administered to a human (one teaspoonful, once or twice daily) as a dietary supplement or as recommended by a health care professional. Alternatively, the dry powder may be mixed with juice, water or food to facilitate administration.

EXAMPLE 2

Three dosage units in powder form, each containing 500 mg of essential active ingredient (e.g an amount of the mixture of Example 1, supra. were prepared from the following ingredients:

| | |
|---|---|
| essential active ingredient | 1500 g |
| starch (Rx-1500) | 300 g |
| magnesium stearate, USP | 39 g |
| colloidal silicic acid | 19.5 g |
| Avicel ® pH 102, q.s. to | 3900 g |

The essential active ingredient was ground through a 0.25 mm sieve opening screen. The powdered active ingredient, with 50% of the total amount of magnesium stearate be used, colloidal silicic acid and Avicel® pH 10.2 were passed through a 40 mesh sieve, mixed for 20 minutes and then slugged. The slugs were broken down by forcing through a screen No. 11, and mixed with the remaining magnesium stearate.

One dosage given orally 1–4 times a day is useful in the relief of immuno-deficiency in adult humans provoked by infective disease, or other etiological causes.

EXAMPLE 3

Three thousand dosage units for oral use, each containing 750 mg of the essential active ingredient, were prepared from the following ingredients:

| | |
|---|---|
| essential active ingredient | 750 g |
| colloidal silicic acid | 30 g |

-continued

| | |
|---|---|
| magnesium stearate USP | 30 g |
| microcrystalline cellulose | 150 g |
| lactose | 90 g |

In accordance with the active ingredient potency, the amount of lactose was adjusted to achieve a weight of 900 mg for each dosage unit. The ingredients were passed through a 40 mesh sieve and mixed for 30 minutes. The powder may be mixed into a drink or inserted into hard gelatin capsules No. 0 and filled using Zanazi, model RV-59 equipment. The capsules should be preserved in airtight, light-resistant containers.

When administered to a human adult suffering from low levels of glutathione (GSH) 1 to 4 dosage units daily, the level is adjusted upward to a normal range.

EXAMPLE 4

A mixture of the following ingredients is formed into a powdered dosage form in the following proportion:

| Ingredient | Quantity |
|---|---|
| Vitamin C (ascorbate) | 1000 mg |
| N-acetyle cysteine | 1500 mg |
| L-Glutamine | 3000 mg |
| N-acetyle d-glucosamine | 500 mg |
| Alpha Lipoic acid (ALA) | 75 mg |
| Quercetin | 75 mg |
| Sylimarine | 100 mg |
| Whey protein | 500 mg |
| Conjugated linoteic acid (CLA) | 500 mg |
| Orange flavor | 380 mg |
| Rice syrup | 1516 mg |
| Malic acid | 7.8 mg |
| Citric acid | 7.8 mg |
| Stevia | 455 mg |
| GI Balance (Probiotic) | 300 mg |

Our studies have shown that the administration of the above dosage unit (one rounded teaspoon) mixed into a liquid 1–4 times (preferably 2 times) a day is useful in the relief of immuno-deficiency in adult humans provoked by infective disease, or other etiological causes. For example, the inventive composition can be used effectively to improve heptatic function e.g. decreased inflamation (ALT) in patients with chronic hepatitis C and patients who are receiving protease inhibitors as part of HAART therapy for HIV. Both groups demonstrated an increase in intra lymphocyte GSH levels after the administration of the inventive composition.

Our studies have shown systemic administration of the composition results in an improvement in T lymphocyte function which correlates directly with an increased intra lymphocyte GSH. In addition, our data demonstrates that the inventive composition and method shifts the T-cell balance from TH2 (allergy producing) to TH1 (viral/tumor killing) and the increases intra lymphocyte GSH correlate directly with decreased levels of IgE the immunoglobulin associated with allergies. Further studies have revealed the following:

Systemic administration of the composition increases natural killer cell function which is considered a primitive first line of cellular immune defense.

Systemic administration of the composition decreases serum cholesterol and triglycerides of between 10 and 20% in patients with a variety of hyperlipidemias and a decrease in myalgias associated with illness and exercise and improved muscle recovery after exercise.

Systemic administration of the composition decreases fatigue in patients suffering from a variety of illnesses including but not limited to chronic viral infections, HIV, hepatitis C, chronic fatigue, immuno deficiency syndrome, immune deficiencies, cancer, B-cell malignancies, including lymphomas, chronic leukemia, myeloma Waldenstrom's and MGUS. This makes the composition function as both a pharmaceutical and a therapeutic substance for patients suffering from the debilitating conditions.

Initial studies have shown that the systemic administration of the inventive composition also increases energy in people without illness who are exposed to increased stress.

As such, the combination formulated will improve hepatic function in conditions associated with chronic viral infections, as well as any condition associated with increased hepatic work or stress.

Thus by the present invention its advantages will be realized and although preferred embodiments have been disclosed and described in detail herein, its scope should not be limited thereby rather its scope should be determined by that of the appended claims.

What is claimed is:

1. A composition of matter, which comprises in admixture;

N-acetylcysteine[;], N-acetyl-d-glucosamine *and* vitamin C whereby the amount of vitamin C is in an amount of at least 1000 mg. or greater to facilitate the absorption of N-acetylcysteine across the cellular membrane; and, a pharmaceutically acceptable carrier for oral administration.

[2. The composition of claim 1 further comprising one or more of the following substances from the group consisting of alpha-lipoic acid, sylmarin, quercitin, 1-glutamine, a probiotic, and dietary protein.]

[3. The composition of claim 1 further comprising alpha-lipoic acid, sylmarin, quercitin, 1-glutamine, and a probiotic.]

[4. The composition of claim 3 further comprising dietary protein.]

[5. The composition of claim 1 further comprising flavorants.]

[6. The systematic administration of a pharmaceutically effective amount of the composition according to claim 1 to a mammal suffering from low glutathione levels, to stimulate the natural production of glutathione in the biologically active cells of the mammal.]

[7. The systemic administration of a pharmaceutically effective amount of the composition according to claim 2 to a mammal suffering from hepatitis, to stimulate the natural production of glutathione in the biologically active cells of the mammal.]

[8. The systemic administration of a pharmaceutically effective amount of the composition according to claim 2 to a mammal suffering from HIV, to stimulate the natural production of glutathione in the biologically active cells of the mammal.]

[9. The systemic administration of a pharmaceutically effective amount of the composition according to claim 2 to a mammal suffering from allergies, to stimulate the natural production of glutathione in the biologically active cells of the mammal and to promote the shift of the T-cell balance from TH2 to TH1 and decrease levels of IgE.]

[10. The systemic administration of a pharmaceutically effective amount of the composition according to claim 2 to a mammal to decrease serum cholesterol and triglycerides.]

[11. The systemic administration of a pharmaceutically effective amount of the composition according to claim 2 to a mammal suffering from one or more of the following illnesses from the group consisting of chronic viral infections: HIV, hepatitis C, chronic fatigue, immuno deficiency syndrome, immune deficiencies, cancer, B-cell malignancies, including lymphomas, chronic leukemia, myeloma Waldenstrom's and MGUS to improve immune defense productions and thereby mitigate the progression of the illnesses to thereby limit fatigue.]

[12. The systemic administration of a pharmaceutically effective amount of the composition according to claim 2 to a mammal to decrease fatigue.]

[13. The systemic administration of a pharmaceutically effective amount of the composition according to claim 2 to a mammal to decrease the biologic effects of stress.]

[14. The systemic administration of a pharmaceutically effective amount of the composition according to claim 2 to a mammal to increase energy and improve physical performance.]

[15. Administration according to claim 6 wherein a pharmaceutically effective amount is 0.1 mg/kg to about 50 mg/kg of body weight of the mammal, daily.]

[16. Administration according to claim 6 wherein a pharmaceutically effective amount is 0.5 mg/kg to about 25 mg/kg of body weight of the mammal, daily.]

[17. The systemic administration of a pharmaceutically effective amount of the composition according to claim 2 to a mammal suffering from low glutathione levels, to stimulate the natural production of glutathione in the biologically active cells of the mammal.]

[18. The systemic administration of a pharmaceutically effective amount of the composition according to claim 3 to a mammal suffering from low glutathione levels, to stimulate the natural production of glutathione in the biologically active cells of the mammal.]

[19. The systemic administration of a pharmaceutically effective amount of the composition according to claim 1 to a mammal suffering from low glutathione levels, to stimulate the natural production of glutathione in the biologically active cells of the mammal and reduce symptoms of diseases caused by excess unneutralized free radicals.]

[20. The systemic administration of a pharmaceutically effective amount of the composition according to claim 2 to a mammal suffering from low glutathione levels, to stimulate the natural production of glutathione in the biologically active cells of the mammal and reduce symptoms of diseases caused by excess unneutralized free radicals.]

[21. The systemic administration of a pharmaceutically effective amount of the composition according to claim 3 to a mammal suffering from low glutathione levels, to stimulate the natural production of glutathione in the biologically active cells of the mammal and reduce symptoms of diseases caused by excess unneutralized free radicals.]

[22. The systemic administration of a pharmaceutically effective amount of the composition according to claim 19, wherein the disease is a member of the group consisting of pulmonary oxygen toxicity, adult respiratory distress syndrome, broncopulmonery dysplasia, sepis syndrome, Parkinson's disease, encephalitis, endotoxemia, anoxia induced neuronal damage, ischemic reperfusion injury, inflammatory diseases, systemic lupus erythematosis, myocardial infarction, stroke, traumatic hemorrhage, spinal cord trauma, Crohn's disease, rheumatoid arthritis, diabetes, cataract formation, uvetis, emphysema, gastric ulcers, oxygen toxicity, neoplasia, undesired cell apoptosis, radiation sickness.]

[23. The systemic administration of a pharmaceutically effective amount of the composition according to claim 20, wherein the disease is a member of the group consisting of pulmonary oxygen toxicity, adult respiratory distress syndrome, broncopulmonery dysplasia, sepis syndrome, Parkinson's disease, encephalitis, endotoxemia, anoxia induced neuronal damage, ischemic reperfusion injury, inflammatory diseases, systemic lupus erythematosis, myocardial infarction, stroke, traumatic hemorrhage, spinal cord trauma, Crohn's disease, rheumatoid arthritis, diabetes, cataract formation, uvetis, emphysema, gastric ulcers, oxygen toxicity, neoplasia, undesired cell apoptosis, radiation sickness.]

[24. The systemic administration of a pharmaceutically effective amount of the composition according to claim 21, wherein the disease is a member of the group consisting of pulmonary oxygen toxicity, adult respiratory distress syndrome, broncopulmonery dysplasia, sepis syndrome, Parkinson's disease, encephalitis, endotoxemia, anoxia induced neuronal damage, ischemic reperfusion injury, inflammatory diseases, systemic lupus erythematosis, myocardial infarction, stroke, traumatic hemorrhage, spinal cord trauma, Crohn's disease, rheumatoid arthritis, diabetes, cataract formation, uvetis, emphysema, gastric ulcers, oxygen toxicity, neoplasia, undesired cell apoptosis, radiation sickness.]

[25. The systemic administration of a pharmaceutically effective amount of the composition according to claim 1 to a mammal, to promote the natural production of glutathione in the biologically active cells of the mammal which accelerates the detoxification of ethanol and alleviates symptoms associated with excessive ethanol imbibation.]

26. The composition of claim 1 further comprising a probiotic, said probiotic for promoting the breakdown and absorption of nutrients, the elimination of toxins and to inhibit the growth of harmful bacteria in the gastrointestinal tract, thereby facilitating the absorption of N-acetylcysteine into the gastrointestinal tract.

27. The [probiotic] *composition* of claim [1] *26*, wherein said probiotic [is a composition of "healthy bacteria" containing] *comprises* one or more [of said healthy] bacteria selected from the group [comprising bifidobacterium longum, bifidobacterium infantis, lactobacillus acidophilus, lactobacillus casei, lactobacillus rhamnosus, saccharomyces boulardi, propionibacteria and enterococci] *consisting of Bifidobacterium longum, Bifidobacterium infantis, Lactobacillus acidophilus, Lactobacillus casei, Lactobacillus rhamnosus, Saccharomyces boulardi, Propionibacteria and Enterococci.*

[28. The composition of claim 2 further comprising 1-glutamine, said component being an essential dietary component to promote the support of gastrointestinal growth and function, thus facilitating the absorption of N-acetylcysteine through the gastrointestinal tract.]

[29. The composition of claim 4 wherein N-acetyl-d-glucosamine promotes the biosynthesis of mucosal glycoproteins which make up the glycocalyx, a layer of the gut mucosa which acts to protect the tissue of the gastrointestinal tract while providing a selectively absorptive surface, thus facilitating the absorption of N-acetylcysteine into the gastrointestinal tracts.]

*30. A method of treatment comprising the step of systemically administering a pharmaceutically effective amount of the composition according to claim 1 to a mammal suffering from low glutathione levels, to stimulate the natural production of glutathione in the biologically active cells of the mammal and reduce symptoms of diseases caused by excess unneutralized free radicals.*

*31. The method of treatment according to claim 30, wherein the disease is a member of the group consisting of pulmonary oxygen toxicity, adult respiratory distress syndrome, bronchopulmonary dysplasia, sepis syndrome, Parkinson's disease, encephalitis, endotoxemia, anoxia induced neuronal damage, ischemic reperfusion injury, inflammatory diseases, systemic lupus erythematosis, myocardial infarction, stroke, traumatic hemorrhage, spinal cord trauma, Crohn's disease, rheumatoid arthritis, diabetes, cataract formation, uveitis, emphysema, gastric ulcers, oxygen toxicity, neoplasia, undesired cell apoptosis, and radiation sickness.*

*32. A method of promoting the biosynthesis of mucosal glycoproteins and/or facilitating the absorption of N-acetylcysteine into a gastrointestinal tract of a mammal, comprising the step of administering the composition of claim 1.*

* * * * *